(12) United States Patent
Brocia

(10) Patent No.: US 7,851,223 B2
(45) Date of Patent: Dec. 14, 2010

(54) METHOD TO DETECT EMPHYSEMA

(75) Inventor: Robert W. Brocia, Bronxville, NY (US)

(73) Assignee: Roar Holding LLC, New York, NY (US)

( * ) Notice: Subject to any disclaimer, the term of this patent is extended or adjusted under 35 U.S.C. 154(b) by 962 days.

(21) Appl. No.: 11/067,367

(22) Filed: Feb. 26, 2005

(65) Prior Publication Data

US 2005/0233401 A1 Oct. 20, 2005

Related U.S. Application Data

(60) Provisional application No. 60/548,837, filed on Feb. 27, 2004.

(51) Int. Cl.
*G01N 33/48* (2006.01)

(52) U.S. Cl. ........................................................ 436/63
(58) Field of Classification Search ........................ None
See application file for complete search history.

(56) References Cited

PUBLICATIONS

Jiang et al. "Expression of plasma phospholipid transfer protein mRNA in normal and emphysematous lungs and regulation by hypoxia", JBC, 1998, 273(25):15714-15718.*
Lumb et al. "Transfer of phospholipids by a protein fraction obtained from canine pulmonary lavage", Biochimica et Biophysica Acta, 1988, 963:549-552.*

* cited by examiner

*Primary Examiner*—Karen Cochrane Carlson
*Assistant Examiner*—Bin Shen
(74) *Attorney, Agent, or Firm*—Morrison & Foerster LLP

(57) ABSTRACT

Methods to detect emphysema by assessing phospholipid transfer protein in lung lavage are described.

10 Claims, 8 Drawing Sheets

METHOD TO DETECT EMPHYSEMA

CROSS-REFERENCE TO RELATED APPLICATIONS

This application claims priority under 35 U.S.C. §119(e) to provisional application 60/548,837 filed 27 Feb. 2004. The contents of this application are incorporated herein by reference.

TECHNICAL FIELD

The invention is directed to improved methods to assay for the activity of phospholipid transfer proteins (PLTP's). Such assays are useful in identifying compounds that various inhibit PLTP's activities and in assessing conditions related to abnormal PLTP activity.

BACKGROUND ART

Several different phospholipid transfer proteins have been identified (Phospholipid transfer proteins from lung, properties and possible physiological functions, Chemistry and Physics of Lipids, Volume 38, Issues 1-2, 30 Aug. 1985, Pages 17-27 Jane D. Funkhouser and Robert J. Readand) these are expressed in different tissues in addition to the more familiar plasma PLTP, which is a 51 kD protein containing 476 amino acid residues and is found mostly in plasma, placenta and pancreas, but is also present in lung, kidney, heart, liver, skeletal muscle, small intestine and brain. For example, two different PLTP's have been found in lung and they differ significantly from the plasma PLTP. (Properties of a non-specific phospholipid-transfer protein purified from rat lung, Biochimica et Biophysica Acta (BBA)—Lipids and Lipid Metabolism, Volume 752, Issue 1, 16 Jun. 1983, Pages 118-126)

The nucleotide sequence encoding of the plasma PLTP has been cloned and sequenced as disclosed in U.S. Pat. No. 5,610,019, the contents of which are incorporated herein by reference. The activity of this protein has been reviewed by Tall, in *An. Rev. Biochem.* (1995) 64:235-237.

Phospholipid transfer proteins facilitate transfer of substrates which include phospholipids, diglycerides and vitamin E from donor unilamellar vessels or lipoproteins into HDL or other lipoproteins. It is also known that the plasma PLTP plays a role in HDL formation and in regulating the secretion of Apo-B containing lipoproteins. Plasma PLTP also plays a role in atherosclerosis development and Cholesteryl ester transfer protein (CETP) activity is enhanced by the plasma PLTP.

With respect to assays for PLTP activity, the above-referenced '019 patent describes a heterogeneous assay where the acceptor is biotinylated HDL. In a study involving assessing the substrate specificity of PLTP, in particular in investigating whether PLTP would interact with LPS, Hailman, E., et al., *J: Biol. Chem.* (1996) 271:12172-12178 describe an assay in which LPS labeled with the fluorophore boron dipyrromethane difluoride (BODIPY) is transferred from self-associated micelles to various acceptors. The authors found that PLTP could mediate the exchange to HDL particles but not to CD14.

Oskolkova, O. V., et al., *Chem. Phys. Lipids* (1999) 99:73-86 employed pyrene conjugates of phospholipid-coupled thymidine to monitor, the spontaneous transfer of thymidine from vesicles to acceptors; high levels of spontaneous transfer were observed.

Pyrene was also used as a label by Huuskonen, J., et al, *Biochem/Biophys. Acta* (1996) 1303:207-214. These authors studied the specificity of the enzyme using pyrene-labeled phospholipids from quenched donor phospholipid vessels to HDL3 particles.

Lalanne, F., et al., *J. Lipid Res.* (2001) 42:142-149, in studying the modulation of transfer of phospholipids by diacylglycerols also employed pyrene-labeled phosphatidylcholine and measured transfer from various types of vesicles to HDL.

While pyrene is often referred to as self-quenching, this is not in fact the case. Pyrene has a monomer/excimer emission profile whereby at low concentrations the monomer fluoresces at 390 nm but at higher concentrations the emission shifts to 470 nm. The ratio of 390/470 intensities is measured; however, this ratio is also dependent on viscosity and temperature. Thus, pyrene is not truly a self-quenching fluorophore.

Nichols, J. W., *Seminars in Cell and Developmental Biology* (2002) 13: 190-184 measured trafficking of phospholipids using N-nitrobenz-2-oxa-1,3-diazol 4-yl (NBD) as label. The paper does not concern an assay for levels of PLTP; rather, the movement of phospholipids in various contexts is measured.

Finally, U.S. patent application Ser. No. 10/279,787, filed Oct. 23, 2002 by this inventor discloses a PLTP activity assay which is improved upon in the current invention.

The measurement of PLTP activity has been handicapped by an extremely high background of spontaneous transfer from donor to acceptor. In addition, many prior art assays are heterogeneous assays and thus require separation of donor from acceptor before measurement is made.

The present invention minimizes the background of spontaneous transfer; in one embodiment, the assay is conducted as a homogeneous assay, thus offering added convenience. The invention further addresses the issue of substrate specificity by providing the ability to measure and express specific transfer rates of various substrates. The invention proves useful in the characterization of diseased states.

DISCLOSURE OF THE INVENTION

The invention is directed to assays for PLTP activity which have improved signal-to-noise ratios and will detect differences in transfer protein activities according to substrate specificity. In one embodiment, the assays are homogeneous assays that permit fewer manipulations and ease of measurement.

Thus, in one aspect, the invention is directed to a method to determine the PLTP activity in a sample which method comprises incubating a reaction mixture containing said sample with donor particles comprising labeled PLTP substrate, which donor particles have aqueous cores and with an acceptor emulsion under conditions of osmotic pressure wherein said donor particle is destabilized and measuring the amount of label incorporated into said acceptor, thus determining the PLTP activity.

In one embodiment, the measuring of the amount of label incorporated into said acceptor is performed on the mixture itself, in a homogeneous assay.

In another aspect, the invention is directed to a kit for conducting the method which comprises a donor particle comprising a labeled PLTP substrate and aqueous core. The kit may also comprise an acceptor emulsion and a solute for enhancing osmotic pressure on the donor particle. The kit will include instructions for conducting the assay.

In other aspects, the invention is directed to screening for defects in the gene encoding one or more types of phospholipids transfer proteins, identifying compounds that modulate different PLTP's activity, assessing medical conditions correlated to different PLTP activities including determining coronary disease risk or organ malfunction.

In all of these applications, the assay method of the invention is employed. For assessment of medical conditions or gene defects, the PLTP's activities in a sample from a subject to be tested is compared to the activities of a sample derived from normal subjects. This value may be prerecorded. In identifying a compound which modulates a specific activity of one or more PLTP's, the activity is compared in the presence and absence of the compound tested.

MODES OF CARRYING OUT THE INVENTION

Figure 1:
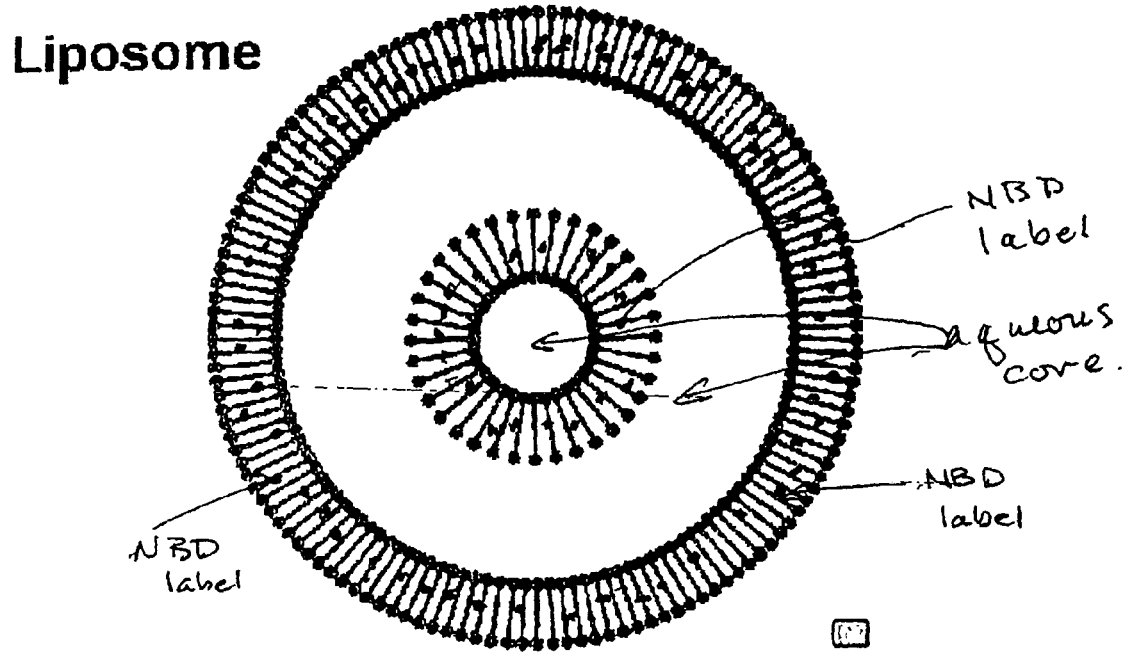
FIG. 1 shows a typical donor particle comprising substrate.

Abnormal PLTP activity has been associated with a number of conditions including hyperlipidemia, increased secretion in levels of Apo-B containing lipoproteins, and heart disease. Abnormal PLTP function can be readily addressed by dietary, pharmaceutical and exercise regimens. Thus, it is important to provide an assay for PLTP activity that is accurate and free of background levels that make interpretation of the results difficult or inaccurate.

The present invention provides an assay which results in a diminution of background readout in comparison to signal. The assay is based on the disruption of a donor particle containing an aqueous core by providing sufficient osmotic pressure to effect such disruption. By modifying the donor particle in this way, spontaneous transfer of the substrate to the acceptor is greatly reduced.

The participants in the assay are the labeled substrate, which represents the moiety to be transferred, a donor particle, which represents the original residence of the substrate, and an acceptor emulsion which is the moiety to which the substrate is transferred.

The substrate for PLTP will be a moiety that the enzyme is capable of transferring. Such moieties include phospholipids such as phosphatidylcholine (PC), phosphatidylethanolamine (PE), phosphatidylinositol (PI), phosphatidylglycerol (PG) and phosphatidylserine (PS) as well as diacylglycerols (DO), sphingomyelin (SM), lipopolysaccharides (LPS) and Vitamin E. Other potential substrates may be tested in the assay of the invention to ascertain their ability to be transferred by one or more types of PLTP.

The donor particle contains a lipid capsule which surrounds one or more aqueous cores. Such moieties are generally known as liposomes and may be unilamellar or multilamellar. It will be noted that the substrate itself may be a member of the hydrophobic layer which makes up the structure of the donor particle. Indeed, the donor particle may be composed entirely of substrates for the PLTP enzyme. The designation of one or another of the components as a substrate is accomplished through labeling.

Thus, the liposomes that behave as donor particles will typically comprise phospholipids such as the above-mentioned substrates but may also include other components such as neutral lipids such as triglycerides and cholesterol. The components of the liposomes may include positively charged lipids, negatively charged lipids and neutral lipids. The ratio of the components, is such that the component designated as a substrate is in excess, if a self-quenching fluorophore is used as label; otherwise the ratio may be more variable. Typically, the ratio of the substrate to additional components of the liposome is of the order of 5:1 to 2:1 in the case of self-quenching labels; other acceptable ratios may be found by routine optimization.

Typical components of the liposomes which behave as donor particles include dipalmitoyl phosphatidylserine (DPPS), distearoyl phosphatidylserine (DSPS), dilauroyl phosphatidylserine (DOPS), dimyristyl phosphatidylserine (DMPS), and the corresponding phospholipids wherein the phosphate moiety is coupled to ethanol, choline, inositol, and the like. This list is merely illustrative and not inclusive.

The acceptor is typically an emulsion comprising particles which are lipid-based and lack an aqueous core or, theoretically, contain an aqueous core of high osmotic pressure. Typical emulsions contain, for example, high density lipoprotein particles or contain micelles formed from triglycerides. The acceptor emulsions may also contain proteins for stability. The characterizing feature of the acceptor, however, is that it is an emulsion wherein the emulsified lipids do not contain aqueous cores.

Preparation of the donor particles is accomplished using standard methods known in the art, such as those described in "Liposomes: Rational Design" (A. S. Janoff, ed., Marcel Dekker, Inc., NY) or by any alternative techniques generally known in the art. Typically, the lipophilic components are dissolved in an organic solvent and sonicated or microfluidized in aqueous buffer. As the substrate is a structural component of the liposome, it is unnecessary to invoke a specific procedure for encapsulation or to provide procedures for removal of unencapsulated material.

The acceptor composition is prepared as an emulsion with a preponderance of neutral lipids, and, preferably, includes some protein as a stabilizing agent. Alternative acceptors include lipoproteins (e.g., HDL, LDL, and VLDL) and a synthetic emulsion similar to lipoproteins comprising, for example, cholesterol 25:mg/dL, protein (casein or Apo-AI) 1 to 15 mg/ml, a phospholipid selected from phosphatidylcholine, phosphatidylethanolamine, phosphatidyl-L-serine, phosphatidylinositol, phosphatidic acid, phosphatidyl-DL-glycerol, lysophosphatidylcholine, sphingomyelin, and cardiolipin at 10 to 200 mg/ml, and triglyceride. These lipids may be present in mass at a range similar to that found in lipoproteins. These emulsions are prepared by sonication or microfluidization as well. Alternatively, commercially available suspensions such as milk or solid forms thereof may be used in suitable dilutions.

Typically, a solution with a concentration of solute effective to generate a desired osmolality is added to the acceptor emulsion prior to mixing with a suspension of the donor particles; however the solute solution may be added at the time of the assay.

The substrate contained in the donor particles comprises a label that will track the progress of the substrate from the donor particle to the acceptor. If the assay is performed in a heterogeneous format, virtually any label can be used since the acceptor and donor particle will ultimately be separated. For example, the acceptor itself might be coupled to a member of a specific binding pair such as an antibody or fragment thereof or biotin and removed from the reaction mixture at various times and the level of label assessed. Thus, in this instance, the substrate may be labeled with a radioisotope, a fluorescent moiety, an enzyme (which then can be assayed using standard enzyme-based assays) or any other suitable label known in the art. Thus, for example, the heterogeneous assays described in U.S. Pat. No. 5,610,019 can be adapted to the method of the invention by substituting for the labeled donor VLDL or LDL, the donor particles of the invention, and adjusting the osmotic pressure. In the assay described in the '019 patent, the acceptor is biotinylated HDL, and the substrate is tritiated phosphatidylcholine. The transfer of the tritiated substrate to acceptor which is separated using streptavidin coupled beads, is measured by scintillation counting. Performing such assays using the donor particles and osmotic pressures of the invention provides superior results due to lowering the level of spontaneous transfer.

However, in a preferred method, the assay is performed in a homogeneous format by taking advantage of the ability of a label to change its properties depending on its environment. A particularly preferred label is a self-quenching fluorescent molecule which, when removed from a concentrated environment exhibits enhanced fluorescence due to the lack of proximity of the fluorescent molecules. Alternatively, the intensity of fluorescence may simply change depending on the environment per se. It is known, for example, that rubidium complexes, p-azophenylarsonate, and fluorescein are quenched when bound to antibodies while antibodies raised against E-dansyllysine enhance the fluorescence of this compound when bound to the antibody. The acceptor emulsion, since it may contain proteins, may include antibodies which are specific for the label or substrate and thus affect the fluorescence properties of the label.

Other examples of moieties whose signal is affected by the environment include clusters of metal atoms known as "quantum dots" whose fluorescence properties are a function of the environment in which they are found. See, for example, U.S. Pat. No. 6,207,392 incorporated herein by reference.

Other labels whose signals are affected by the environment include materials which exhibit nuclear magnetic resonance, where exposure to aqueous environments greatly affects with signal produced.

Thus, for use in a homogeneous assay, the label coupled to substrate will be such that its signal is altered when it passes from donor particle to the acceptor emulsion. Preferred are self-quenching fluorescent labels, such as dansyl, rhodamine, fluorescein, BODIPY, and the like.

A particularly preferred label is the fluorescent self-quenching moiety nitrobenz-2-oxa-1,3-diazol-4-yl (NBD) which can be readily coupled to phospholipids, such as phosphatidylethanolamine, to provide the substrate NBD-PE.

Figure 4:
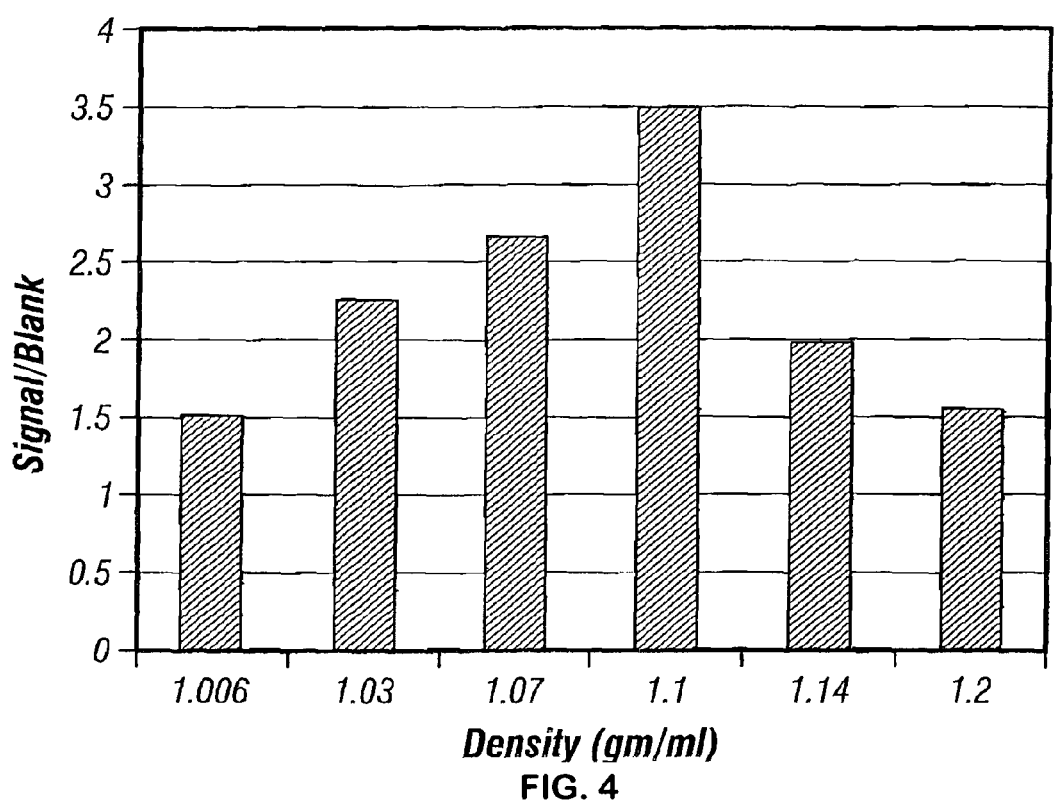
FIG. 4 is a graph indicating the ratio of fluorescence units observed in the presence of PLTP as compared to its absence as a function of the osmotic pressure of the reaction mixture.
Figure 5:
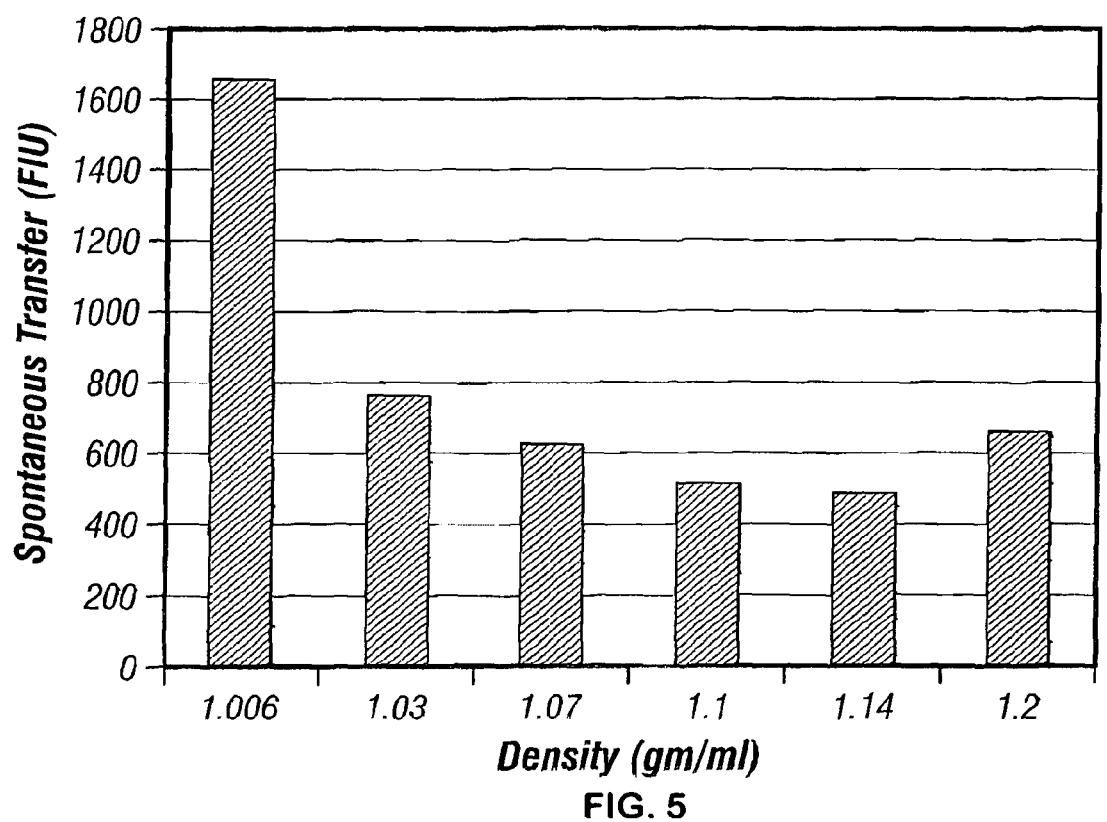
FIG. 5 is a graph showing the fluorescence units generated by spontaneous transfer of substrate to acceptor as a function of osmotic pressure.

To conduct the assay, a suspension of the donor particles in buffer is contacted with the acceptor emulsion and with a solution of solute which provides an osmolality which is equivalent to that provided by a solution containing sodium bromide at a density in the range of 1.05-1.15 g/ml. It appears that at this level of osmotic pressure, optimum signal-to-noise results are obtained (FIG. 4) with the lowest spontaneous transfer (FIG. 5).

Particularly preferred as an osmotic pressure equivalent to that exerted by a 1.1 g/ml solution of sodium bromide (which has an osmolality of 2.67). Thus, osmolalities of 2.5-2.7 are preferred (FIG. 4, 5).

While the osmolality of the solution is described in terms of the density of sodium bromide solutions, any ionic salt may be used to generate similar osmotic pressures. Thus, potassium bromide, sodium chloride, sodium bromide, and other halides as well as soluble sulfates or phosphates could also be used. Sodium bromide and potassium bromide are preferred.

Figure 3:
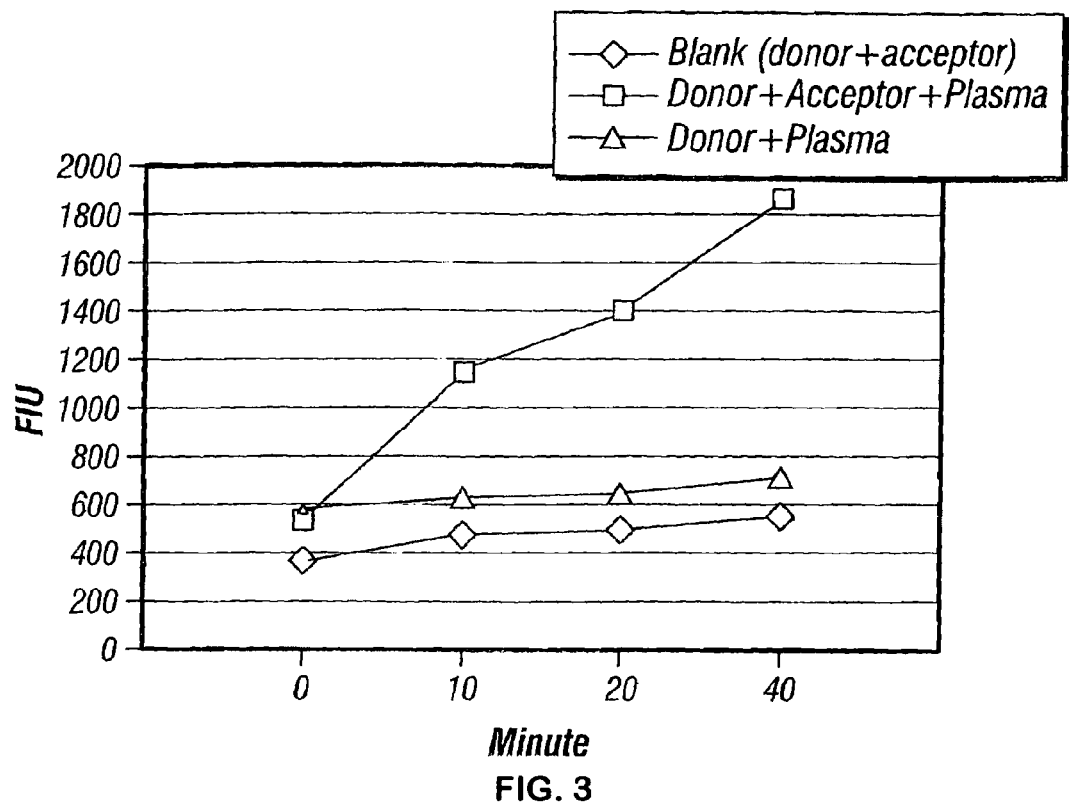
FIG. 3 is a graph showing the time course of substrate transfer using plasma as a source of PLTP.

Thus, a solution of sodium chloride, sodium bromide, or other salts capable of conferring similar osmotic pressures is added to a reaction mixture of sample, donor particles and acceptor emulsion suspended in buffer at an amount sufficient to provide the requisite osmotic pressure; alternatively, the salt solution may be included in the acceptor composition. The donor particles and acceptor emulsion, all in buffer solution, are maintained at the appropriate osmotic pressure for sufficient time to effect transfer, typically about 5-30 minutes, preferably 8-20 minutes, at about 30-37° C. The transfer can be monitored by the transfer of label as described above at various times after mixing. The signal is monitored in a manner appropriate to the choice of label; in a preferred embodiment (FIG. 3), the enhancement of fluorescence of a self-quenched label is measured in a homogeneous assay.

The transfer of label can be compared in the presence and absence of a compound which is a candidate for modulating the activity of PLTP; a diminution or enhancement of transfer in the presence as compared to the absence of such compound identifies it as a modulator. Similarly, a diminution or enhancement of PLTP activity in a test sample, as compared to a standard, indicates a discrepancy between the standard and the test sample. If the standard comprises activity present in biological samples from a normal subject or a population of subjects, the deviation in the test sample indicates an abnormality in the subject from which the sample is taken.

Figure 2:
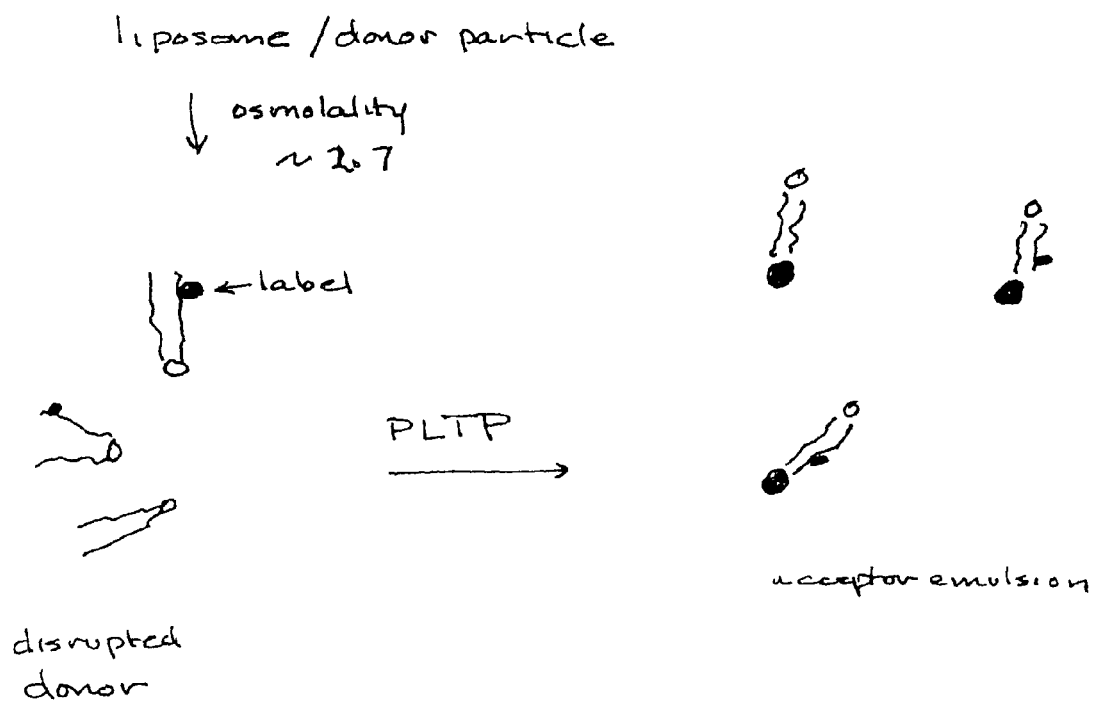
FIG. 2 shows a schematic representation of the PLTP assay.

The general principles of one embodiment of the assay are shown in FIGS. 1 and 2. FIG. 1 is simply a schematic of a liposome indicating that the substrate component of the lipid bilayer is associated with a label. FIG. 2 shows the transfer of the labeled substrate to the acceptor emulsion in the presence of PLTP. As seen, upon providing osmotic pressure to the buffer in which the donor particles and receptor reside, the labeled substrate is transferred in a reaction catalyzed by PLTP to the acceptor emulsion which results in enhancement of fluorescence.

The components useful in the invention can be provided in the form of a kit which contains at least a container which provides labeled donor particles either suspended in buffer or lyophilized and, optionally, a container which contains a buffer solution of acceptor at a tonicity which will provide the appropriate osmolality when mixed with the donor particles in the reaction mixture. Also included is a set of instructions for conducting the assay. If desired, only the container of labeled donor particles may be provided, along with instructions for the preparation of the acceptor emulsion and the osmotic pressure-conferring material. As the acceptor suspension may be prepared from simple materials, such as milk, and as the salts for obtaining the suitable osmotic pressure are readily available, it may be adequate to provide the user simply with instructions for addition of these components.

APPLICATIONS

The assay of the present invention may be used to assess a medical condition; these conditions include but are not limited to diseases of the lung, hyperlipidemia, increased secretion and levels of ApoB-containing lipoproteins, and risk factors for coronary disease. These conditions may be treated with agents affecting plasma PLTP activity or the activity of a PLTP other than the plasma protein.

The assay is performed on a biological fluid derived from a test subject. As used herein, "biological fluid" refers to fluids derived from a subject which are expected to contain PLTP, or are fluids which are extracts from biopsied organs which may be expected to contain PLTP. Most conveniently, the assays are performed on plasma or serum. However, other biological fluids may be used, such as lung lavage, depending on the interest of the experimenter. Any vertebrate subject of interest may be used as a source of biological fluid; most commonly, the assays will be performed on human samples; however, the assay is also useful in determining these levels in other animals such as livestock, companion animals, zoo animals, and other species subject to veterinary care.

As an example, a dietary modification regimen may be prescribed by a health care professional that directly affects the induction, activity, transcription or translation of PLTP. A baseline PLTP value is determined for a subject using the methods and kits described herein; this is compared to a pre-determined range of values considered normal for the subject's species, phenotype, age, gender, and/or genotype. Where the subject's PLTP value is outside the norm, a treatment affecting PL TP activity is recommended, which may comprise dietary modification regimen, a compound that modulates PLTP activity, a compound that affects the transcription/translation of the PLTP gene, an exercise regimen, or combination thereof. The treatment is monitored by assessing the PL TP values in the subject over time. The treatment may be altered according to these results.

Thus, the application of the assay method during a course of treatment of a subject evaluates the ability of the treatment to control the levels and/or activity of PLTP in the subject. The treatment may be effective through inhibition or enhancement of the activity of PLTP, or by inhibition or enhancement of the production of this enzyme. If the latter, the treatment may operate through controlling transcription of the gene encoding this protein or translation of the resulting RNA or both.

The ability of a compound or protocol to modulate the activity of PLTP may also be determined in vitro by conducting the assay in the presence and absence of this compound as described above. The effect of the compound on the activity of a known level of PLTP will identify it as an inhibitor or enhancer of activity.

The following examples are offered to illustrate but not to limit the invention.

Example 1

Determination of PLTP in Standard Samples

The donor particles are comprised of unlabeled phosphatidylcholine (PC) and labeled phospholipid substrates. One, two, three or more donor types may be employed in order to measure different substrate enzyme specificities.

For example, donor A may include, phosphatidylethanolamine (PE) coupled to NBD or NBD-PE; while donor B may include, 1-Oleoyl-2-[6-[(7-nitro-2-1,3-benzoxadiazol-4-yl) amino]hexanoyl]-sn-Glycero-3-[Phospho-rac-(1-glycerol)] (NBD-PG); and, donor C may include, 1-Palmitoyl-2-[6-[(7-nitro-2-1,3-benzoxadiazol-4-yl)amino]hexanoyl]-sn-Glycero-3-Phosphocholine (NBD-PC).

The molar ratio of NBD labeled substrate to the remainder of the unlabeled phospholipid, PC, must be >50% to permit sufficient self-quenching.

The three compositions of donor particles were prepared:

Composition donor A: 10 mg NBD-PE+2.00 mg PC

Composition donor B: 10 mg NBD-PC+2.45 mg PC

Composition donor C: 10 mg NBD-PG+2.38 mg PC

Mixtures containing Composition A and Composition B and Composition B are dissolved in chloroform and dried under argon. Traces of solvent were removed under vacuum.

To each vessel containing each composition was added 10, 12.25 and 11.9 ml buffer solution (10 mM Trizma/150 mM saline/pH 7.4+1 mM EDT A), respectively. The mixtures were sonicated for 30 minutes at 30° C. and centrifuged to remove any particulates, and the suspended donor particles were stored at 25° C. after a final dilution of 1:3 with buffer.

Figure 6:
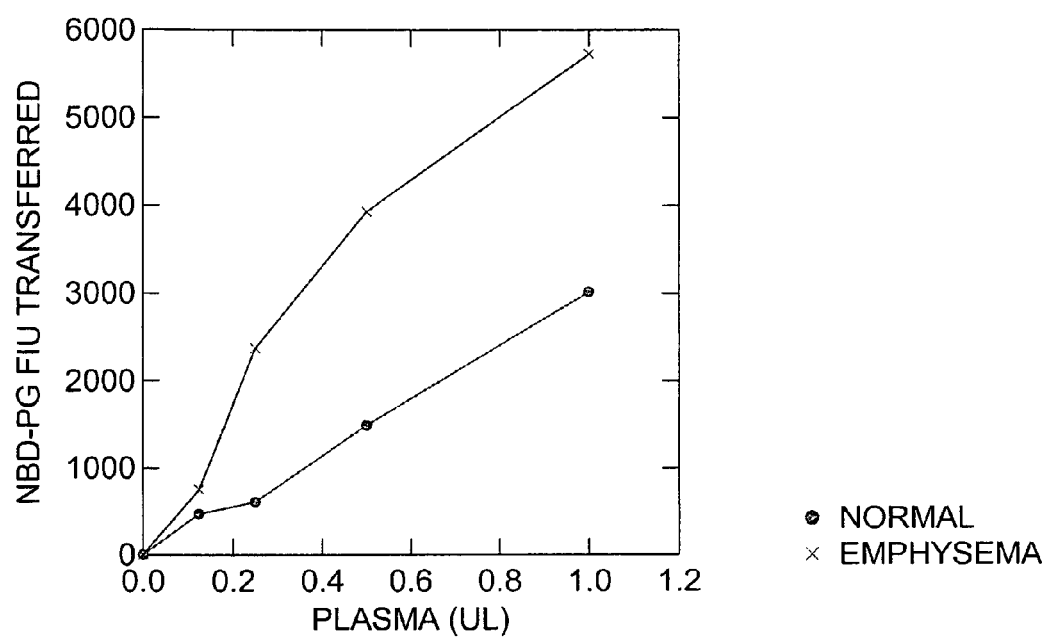
FIG. 6 is a graph comparing normal human plasma versus emphysema patient plasma transfer of one substrate.
Figure 7:
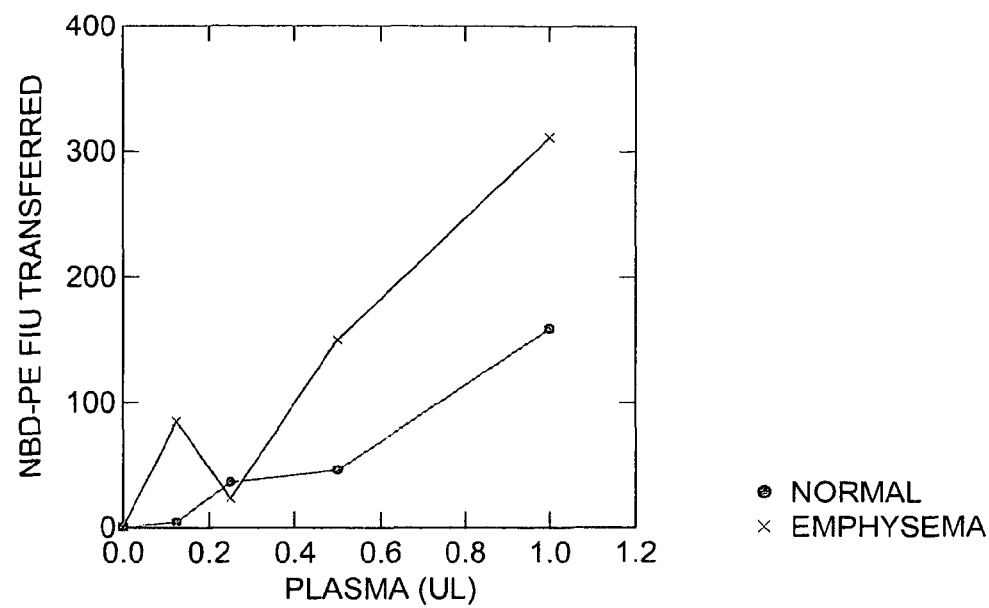
FIG. 7 is a graph comparing normal human plasma versus emphysema patient plasma transfer of another substrate.
Figure 8:
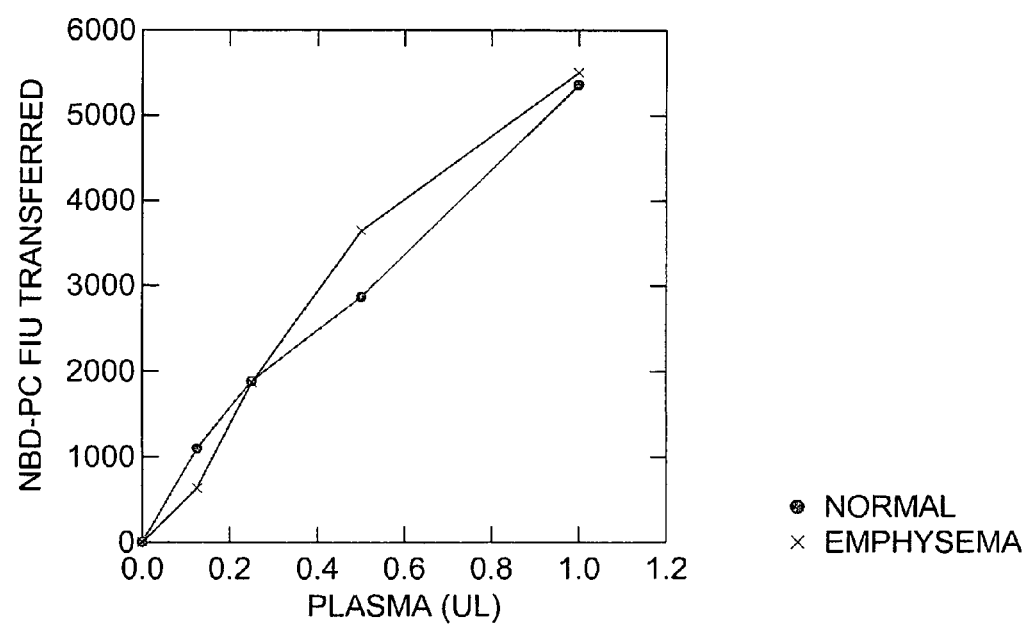
FIG. 8 is a graph comparing normal human plasma versus emphysema patient plasma transfer of a third substrate.

In the assays below, the donor particles derived from composition A, B and C were used. The reaction mixture contains 50 ul acceptor emulsion; 3 ul of the donor particle preparation, 42 ul of assay buffer (10 mM Trizma/150 mM NaCl/1 mM EDT A) and 10 ul of plasma diluted 1:10 with serial dilutions to deliver 1, 0.5, 0.25, 0.125 ul of plasma to each assay and both normal human plasma and emphysema patient plasma was tested. The transferred fluorescence intensity was calculated by subtracting a buffer blank assay. Incubations were at 37° C. for 10 minutes and the assays fluorescence is read using an excitation wavelength of 465 nm and an emission wavelength of 535 nm. The results are shown in FIGS. 6, 7 and 8 for donors of compositions C, A and B, respectively.

The normal patient plasma is, according to the invention, less active at transferring NBD-PG (FIG. 6) and NBD-PE (FIG. 7) than the emphysema patient plasma. However, the transfer of NBD-PC (FIG. 8) in both patient plasmas is very similar.

Figure 9:
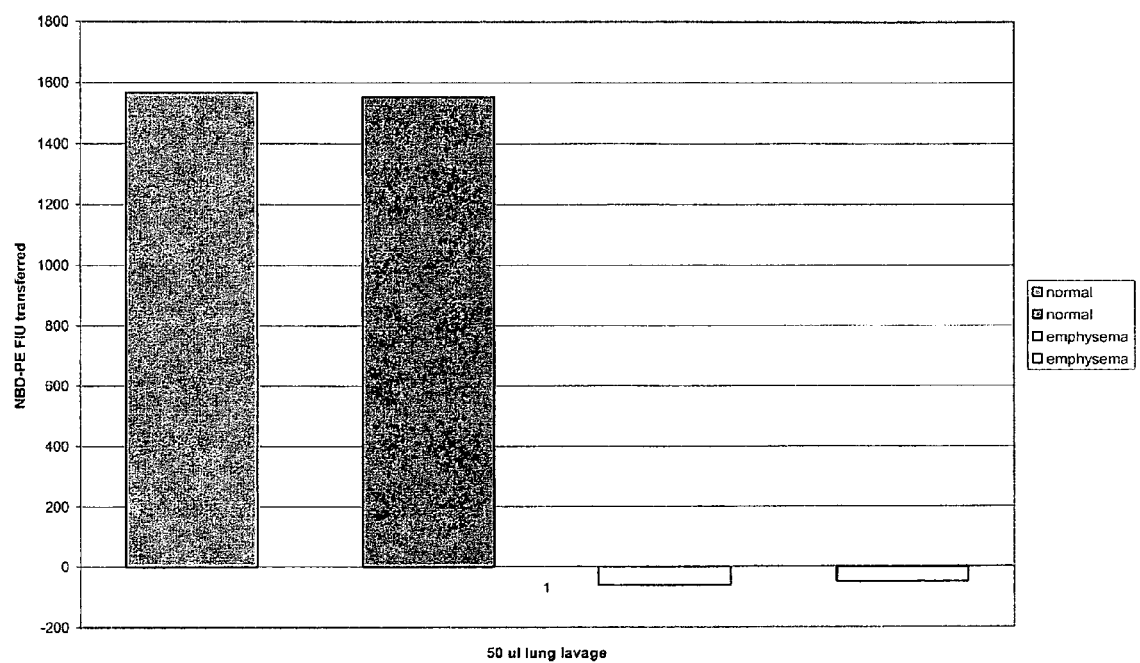
FIG. 9 is a graph comparing normal human lung lavage versus emphysema patient lung lavage transferring one substrate.

FIG. 9 illustrates a dramatically different result when lung lavage is tested in the invention. Saline washes were tested from both normal and emphysema patients with the normal lung lavage samples showing significant NBD-PE transfer activity while the emphysema samples are completely inactive. Therefore, the invention is useful for diagnosis of diseases or abnormalities by measuring plasma, lung lavage, semen or other bodily fluid.

The assays are performed using, as an acceptor, a mixture which is defined herein as a triglyceride emulsion (TGE). This acceptor comprises a 1:1 mixture with 1.4 g/ml NaBr of a sonicated emulsion which contains 25 mg/dl cholesterol; 5 mg/ml casein; 140 mg/dl phospholipid, and 700 mg/dl triglyceride.

APPLICATION OF STANDARD CURVE TO EXPERIMENTAL DATA

The fluorescence intensity (Y) of a sample of donor dispersed in isopropanol is plotted against picomoles (X) of substrate contained within the donor to obtain a standard curve. Regression analysis indicates high correlation to a straight-line relationship between concentration of NBD labeled substrate dispersed in isopropanol and fluorescence intensity units. A Y intercept and slope for the standard curve are calculated, thus permitting a calculation to be made of total number of picomoles transferred from fluorescence intensity units (FIU) transferred during the assay incubation.

Applying the standard curve determined by dispersing the appropriate donor particle in isopropanol a value representing the picomoles of NBD labeled substrate transferred in the sample can be calculated. For example, at the desired time point, the FIU reading may be 1900; the average blank reading may be 600, thus providing a transferred FIU value due to the catalyzed transfer of approximately 1300. Applying the linear equation, a value of picomoles transferred of substrate by the sample during the incubation is obtained.

I claim:

1. A method to determine the presence or absence of emphysema in a test subject, which method comprises determining the activity of phospholipid transfer protein (PLTP) in a sample of lung lavage of said subject wherein a substantial absence of PLTP activity in said sample when compared to normal control indicates the presence of emphysema in said subject.

2. The method of claim 1, which further comprises comparing said activity to activity characteristic of a normal subject.

3. The method of claim 1, wherein said determining comprises incubating said sample in a reaction mixture which comprises
   (1) a buffer medium comprising donor particles which donor particles comprise labeled PLTP substrate and an aqueous core,
   (2) an acceptor emulsion to which the substrate may be transferred, and
   (3) sufficient concentration of salt to effect disruption of said donor particles,
   for a time sufficient to effect transfer of said substrate from the donor particles to the acceptor, and
   determining the amount of label incorporated into said acceptor, whereby the activity of PLTP in the sample is determined.

4. The method of claim 3, wherein said determining of the amount of label incorporated into the acceptor is performed on the reaction mixture without separating the acceptor from said reaction mixture.

5. The method of claim 4, wherein said label is a self-quenching fluorescent molecule.

6. The method of claim 5, wherein said label is N-(7-nitrobenz-2-oxa-1,3-diazol-4-yl) (NBD), fluorescein, dansyl, BODIPY, or rhodamine.

7. The method of claim 6, wherein the label is NBD.

8. The method of claim 3, wherein the acceptor emulsion is of high density lipoprotein (HDL).

9. The method of claim 8, wherein said acceptor emulsion comprises cholesterol, protein, phospholipid and triglyceride.

10. The method of claim 3, wherein said concentration of salt provides an osmotic pressure equivalent to that provided by 1.05-1.15 g/ml of NaBr.

* * * * *